United States Patent [19]

Novick et al.

[11] Patent Number: 5,221,789

[45] Date of Patent: Jun. 22, 1993

[54] INTERFERON-GAMMA RECEPTOR FRAGMENT AND ITS PRODUCTION

[75] Inventors: Daniela Novick, Rehovot; Menachem Rubinstein, Givat Shmuel, both of Israel

[73] Assignee: Yeda Research and Development Co. Ltd., Rehovot, Israel

[21] Appl. No.: 578,826

[22] Filed: Sep. 7, 1990

[30] Foreign Application Priority Data

Sep. 7, 1989 [IL] Israel .......................................... 91562

[51] Int. Cl.$^5$ ........................... C07K 3/02; C07K 3/20; C07K 3/22
[52] U.S. Cl. ..................................... 530/350; 530/351; 530/413; 530/416; 530/834
[58] Field of Search ............... 530/350, 412, 413, 416, 530/834, 351; 424/85.5

[56] References Cited

U.S. PATENT DOCUMENTS 4,485,017  11/1984  Tan et al. ............................. 530/413
4,897,264  1/1990  Novick et al. ....................... 424/85.5

FOREIGN PATENT DOCUMENTS

WO9116431  10/1991  PCT Int'l Appl. .

OTHER PUBLICATIONS

Novick et al. J. Chromatography, vol. 510, pp. 331-337, Jun. 1990.
Novick et al. J. Exp. Med., vol. 170 No. 4, pp. 1409-1414, Oct. 1989.
Aguet, et al.; Cell, 55:273-280 (1988); Molecular Cloning and Expression of the Human Interferon-Receptor.

Primary Examiner—Jeffrey E. Russel
Attorney, Agent, or Firm—Iver P. Cooper

[57] ABSTRACT

Soluble human IFN-gamma receptor extracellular fragment and salts, functional derivatives, precursors and active fractions thereof are provided in substantially purified form. They are useful as pharmaceutically active substances for protecting against the deleterious effects of IFN-gamma, e.g. in autoimmune diseases.

4 Claims, 3 Drawing Sheets

FIG. 2

```
  1  MALLFLLPLV MQGVSRAEMG TADLGPSSVP TPTNVTIESY NMNPIVYWEY
 51  QIMPQVPVFT VEVKNYGVKN SEWIDACINI SHHYCNISDH VGDPSNSLWV
101  RVKARVGQKE SAYAKSEEFA VCRDGKIGPP KLDIRKEEKQ IMIDIFHPSV
151  FVNGDEQEVD YDPETTCYIR VYNVYVRMNG SEIQYKILTQ KEDDCDEIQC
201  QLAIPVSSLN SQYCVSAEGV LHVWGVTTEK SKEVCITIFN SSIKGSLWIP
251  VVAALLLFLV LSLVFICFYI KKINPLKEKS IILPKSLISV VRSATLETKP
301  ESKYVSLITS YQPFSLEKEV VCEEPLSPAT VPGMHTEDNP GKVEHTEELS
351  SITEVVTTEE NIPDVVPGSH LTPIERESSS PLSSNQSEPG SIALNSYHSR
401  NCSESDHSRN GFDTDSSCLE SHSSLSDSEF PPNNKGEIKT EGQELITVIK
451  APTSFGYDKP HVLVDLLVDD SGKESLIGYR PTEDSKEFS*
```

FIG. 3

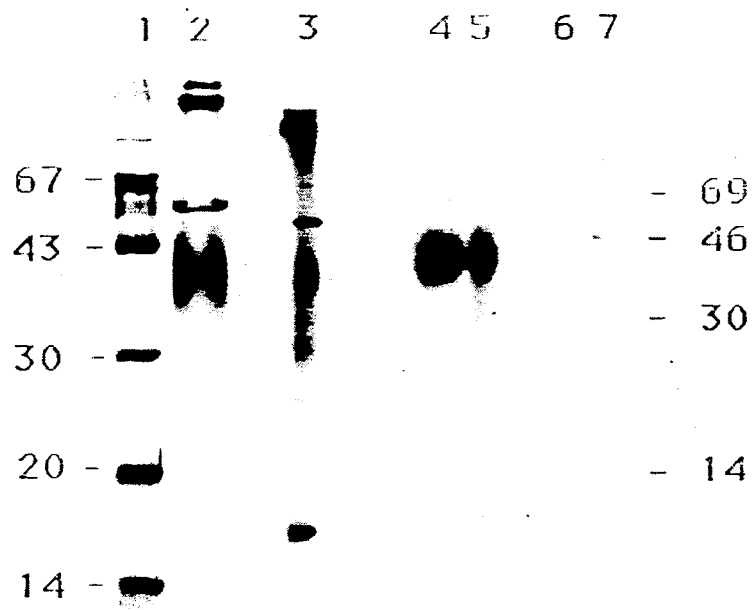

IFN-γ COLUMN ELUATE (μg/ml)

IFN-γ COLUMN ELUATE (μg/ml)

INTERFERON-GAMMA RECEPTOR FRAGMENT AND ITS PRODUCTION

FIELD OF THE INVENTION

This invention relates to substantially purified soluble human interferon gamma (herein IFN-gamma) receptor extracellular fragment and salts, functional derivatives, precursors and active fractions thereof. The invention also relates to a process for the obtention of said human IFN-gamma receptor soluble extracellular fragment from human urine and its purification, to its cloning and its production by recombinant DNA techniques. It further relates to pharmaceutical compositions comprising the soluble human IFN-gamma receptor extracellular fragment, or salts, functional derivatives, precursors and active fractions thereof.

BACKGROUND OF THE INVENTION

Interferon-gamma is a lymphokine produced by activated T-lymphocytes and by large granular lymphocytes. It has antiviral, antitumor and immunomodulatory activities and is of potential clinical value. However, together with its positive biological activities, IFN-gamma has been shown to provoke undesirable effects and to be involved in the development of autoimmune diseases. Thus, IFN-gamma was present in newly diagnosed diabetic children and in muscle biopsies from patients with polymyositis. It was also found to cause exacerbation of autoimmune diseases such as multiple sclerosis and psoriasis.

It is therefore necessary to find ways to eliminate or antagonize the undesirable activities or effects of IFN-gamma endogenously formed in excess or exogenously administered, and particularly to block its action for controlling the progression of autoimmune processes.

In U.S. Pat. No. 4,897,264 of the same applicant three different types of human IFN-gamma receptors were described. The various receptors were isolated from different cells by extraction followed by affinity chromatography on an immobilized IFN-gamma column. The receptors were shown to bind IFN-gamma. They were further used as antigens to immunize mice for the obtention of polyclonal antibodies that blocked selectively the binding of IFN-gamma to some cells and not to others. They may also be used alone or together with the antibodies and/or IFN-gamma as immunosuppressants in autoimmune diseases. In U.S. Ser. No. 07/436,328, now abandoned monoclonal antibodies against the human IFN-gamma receptor were disclosed which blocked the binding of IFN-gamma to its receptor and inhibited the biological activity of IFN-gamma.

One of the effective ways of neutralizing the activity of a hormone or cytokine is to provide a soluble form of its receptor, that binds the protein outside the cell and blocks its activity. It is not necessary to use the whole receptor. A fragment of the receptor which contains the binding-site of the hormone or cytokine, e.g. an extracellular soluble fragment of the receptor will be able to block effectively its biological activity.

SUMMARY OF THE INVENTION

The present invention provides now soluble human IFN-gamma receptor extracellular fragment obtained from human urine and salts, functional derivatives, precursors and active fractions thereof, which can antagonize the effects of and serve as natural blocker of IFN-gamma. It further relates to said extracellular fragment in substantially purified form, being free of proteinaceous impurities, and to a process for its purification.

The invention is also directed to recombinant DNA molecules comprising the nucleotide sequence coding for the human IFN-gamma receptor soluble extracellular fragment, expression vehicles comprising them and host cells transformed therewith, and to a process for producing human IFN-gamma receptor soluble extracellular fragment by culturing said transformant cells in a suitable culture medium and harvesting the human IFN-gamma receptor soluble extracellular fragment either from the cells or from the culture supernatant.

The soluble human IFN-gamma receptor extracellular fragment of the invention and salts, functional derivatives, precursors and active fractions thereof are for use as active ingredients of pharmaceutical compositions to protect mammals against undersirable effects of IFN-gamma.

The soluble extracellular fragment of the IFN-gamma receptor is found in human urine. The substantially purified protein, which is substantially free of proteinaceous impurities, has a molecular weight of about 40K when analyzed by SDS-PAGE under non-reducing conditions. It moves as a single peak on reversed-phase HPLC.

As used herein the term "salts" refers to both salts of carboxyl groups and to acid addition salts of amino groups of the protein molecule. "Functional derivatives" as used herein covers derivatives which may be prepared from the functional groups which occur as side chains on the residues or the N- or C- terminal groups, by means known in the art. "Precursors" are compounds formed prior to, and converted into the IFN-gamma receptor fragment in the animal or human body. "Active fractions" of the substantially purified protein covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has the ability to bind IFN-gamma and to inhibit its undersirable effects.

In a preferred embodiment of the invention, the substantially purified soluble extracellular fragment of the IFN-gamma receptor of the invention is produced by a process which comprises:

a) recovering the crude protein fraction from a dialyzed concentrate of human urine;

b) subjecting said crude protein fraction of step (a) to affinity purification on a column of immobilized IFN-gamma or on a column of immobilized anti-IFN-gamma receptor monoclonal antibody; and c) recovering said substantially purified protein of step (b) having a molecular weight of about 40K on SDS PAGE under non-reducing conditions. When applied to reversed phase HPLC, the protein moves as a single peak.

In a preferred embodiment, the crude protein fraction of step (a) is subjected first to ion exchange chromatography, for example on a carboxymethyl Sepharose (CM-Sepharose) or a DEAE-cellulose column.

In another preferred embodiment, the material obtained in step (b) from a column of immobilized anti-IFN-gamma receptor monoclonal antibody is further purified by applying it to a column of immobilized IFN-gamma.

BRIEF DESCRIPTION OF THE DRAWINGS

FIG. 2 shows (underlined) a major amino acid sequence corresponding to positions 54-70 of the cell surface receptor of human interferon-gamma.

FIG. 3 shows SDS-PAGE analysis of purified preparations prepared according to Example 3.

DETAILED DESCRIPTION OF THE INVENTION

Figure 1:
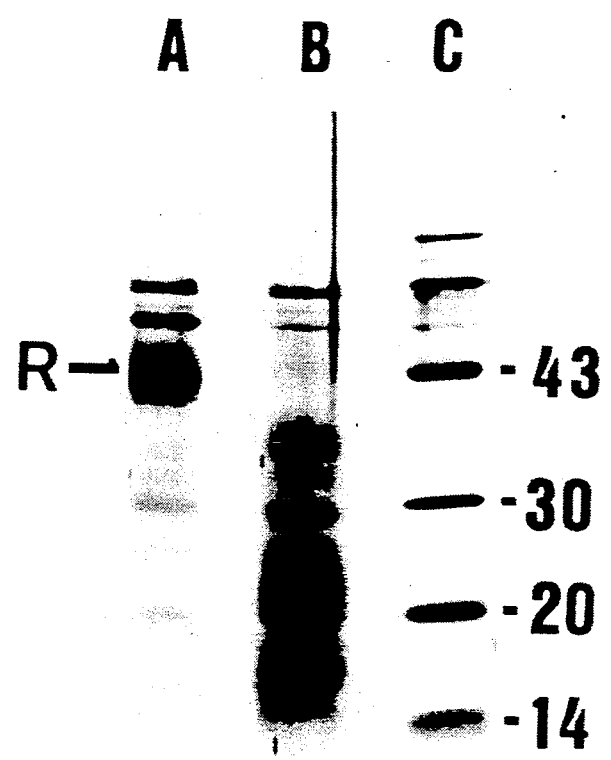
FIG. 1 shows SDS-PAGE analysis of interferon-gamma receptor obtained in Example 3.
Figure 4A:
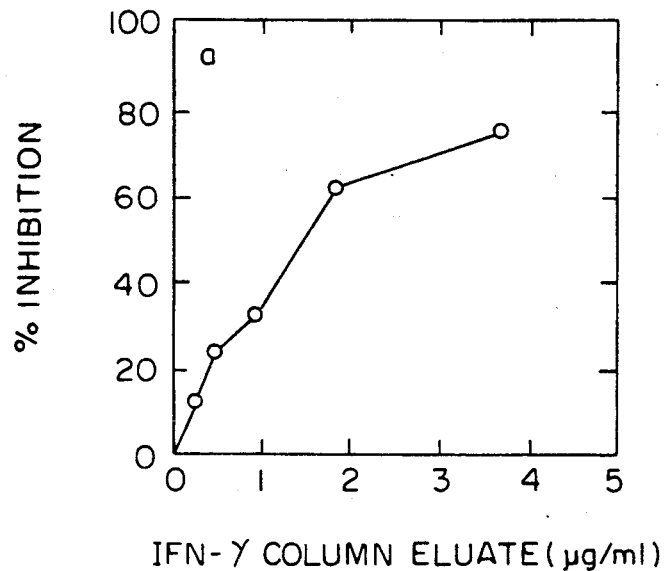
FIG. 4a illustrates inhibition of $^{125}$I-IFN-gamma binding in solid phase RIA to its monoclonal antibody by the IFN-gamma binding protein of the eluate of Example 3.1.
Figure 4B:
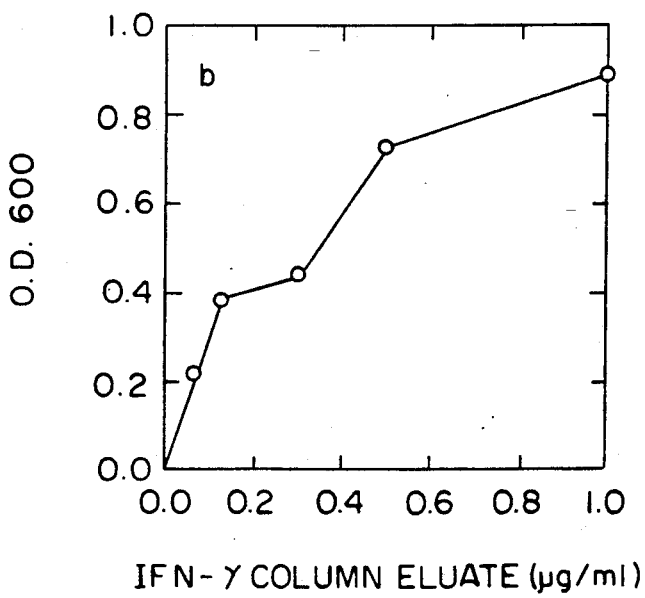
FIG. 4b shows the characterization of the IFN-gamma binding protein of the eluate of Example 3.1 as IFN-gamma receptor by a double-antibody ELISA.

The invention will be further illustrated by way of the following non-limiting examples.

EXAMPLE 1

Preparation of the Urine Concentrate

A pool of 200 liter male urine from healthy donors was subjected to microfiltration on a Pellicon membrane with a pore size of 0.45 μm. The filtrate was concentrated by ultrafiltration using a Pellicon membrane with a molecular weight cut off of 10K to a final volume of 500 ml. The concentrate was dialyzed against phosphate buffered saline (PBS) containing 1 mM benzamidine and 0.1% sodium azide.

EXAMPLE 2

Ion-Exchange Chromatography of the Urine Concentrate on CM-Sepharose

A CM-Sepharose (Pharmacia, Uppsala, Sweden) cation exchange column (2.7×10 cm) was prewashed with 1M NaCl, 10 mM citric acid pH 5.0, containing 0.02% NaN$_3$ (buffer C) and equilibrated with 10 mM citric acid (pH 5) containing 0.02% NaN$_3$ (buffer A). The concentrate of urinary proteins was dialyzed against buffer A and centrifuged, and the supernatant was applied at 4° C. on the column. The column was washed with buffer A, eluted first with 250 ml of a solution containing 200 mM NaCl, 10 mM citric acid (pH 5.0) and 0.02% NaN$_3$ (buffer B) and then with 150 ml buffer C. Fractions of 50 ml were collected and tested for IFN-gamma binding activity (binding of $^{125}$I-IFN-gamma) and their protein concentration was determined.

When a DEAE-cellulose column is used, the elution is performed with a gradient of salt (0-0.5M) or at 10 mM phosphate buffer pH 7.0.

EXAMPLE 3

Affinity Chromatography and Purification of the IFN-gamma Receptor Extracellular Fragment 3.1 Ligand affinity chromatography on immobilized IFN-gamma column Recombinant IFN-gamma from chinese hamster ovary cells was brought to a concentration of 3 mg/ml, then equilibrated with PBS containing 0.02% sodium azide and coupled to Affigel-10 (2.5 mg to 0.5 ml beads). The concentrate of urinary proteins of example 1 or 2 was applied to the IFN-gamma Affigel-10 column at a flow rate of 0.2 ml/min. at 4° C. Following washings with PBS, bound proteins were eluted by applying a solution of citric acid (25 mM, pH 2.5) and immediately neutralized.

3.2 Immunoaffinity chromatography on immobilized anti-IFN-gamma receptor monoclonal antibody column Anti-IFN-gamma receptor monoclonal antibody No. 177-1 disclosed in U.S. Ser. No. 07/436,328, now abandoned, and deposited with the Collection Nationale de Cultures de Microorganismes, Paris, France, under No. CNCM I-814 on 14th November 1988, was coupled to agarose-polyacrylhydrazide (4.5 mg to 0.5 ml beads). The concentrate of urinary proteins of example 1 or 2 was applied to the immobilized antibody agarose column at 4° C. at a flow rate of 0.2 ml/min. Following washings with PBS, bound proteins were eluted with citric acid (25 mM, pH 2.5) and immediately neutralized.

3.3 Tandem affinity chromatography with immobilized anti-IFN-gamma receptor monoclonal antibody and immobilized IFN-gamma The material obtained in Example 3.2 (360 μg) was loaded on immobilized interferon-gamma coupled to agarose (1 ml, containing 2.5 mg bound interferon-gamma). The column was washed with PBS (35 ml) and bound proteins were then eluted with 25 mM citric acid, pH2. Eluted fractions (1 ml) were immediately neutralized with 1M Hepes and analyzed by SDS-PAGE. Fractions 2-5 containing the majority of the soluble interferon-gamma receptor (32 μg) were combined, SDS was added (0.2% final) and the sample was concentrated on a YM-10 membrane (centricon-10, Amicon USA) to a final volume of 125 μl and a total of 20 μg protein. An aliquot (130 ng) of this preparation was analyzed by SDS-PAGE and gave a major broad band of Mr 40,000 under reducing conditions (FIG. 1, lane A).

3.4 CNBr cleavage and amino acid sequence analysis

The preparation of the soluble interferon-gamma receptor fragment of Example 3.3 (5 μg) was brought to 70% formic acid and CNBr was added to a final concentration of 20 mg/ml. The mixture was left overnight in the dark and then lyophilized with several exchanges of water to ensure a complete removal of CNBr and formic acid.

The lyophilized material was subjected to SDS-PAGE under reducing conditions. The gel was then electroblotted onto a PVDF membrane (Immobilon, Millipore 0.45 μ) and stained with Coomassie Blue according to Moos et al (Moos et al., 1988, J.Biol.Chem 263, 6005-6008). Another aliquot of the cleaved receptor (1 μg) was analyzed by SDS-PAGE silver staining (FIG. 1, lane B). As can be seen, 4 distinct bands of molecular weights 35,000, 30,000, 20,000-26,000 and 14,000-18,000 were obtained. The band corresponding to MW 20,000-26,000 was excized from the PVDF membrane and subjected to protein microsequencing according to Matsudaira (Matsudaira, P., 1987, J.Biol.Chem., 262, 10035-10038) showing a major amino acid sequence corresponding to positions 54-70 of the cell surface receptor of human interferon-gamma (Aguet, M. et al., 1988, Cell, 55, 273) (FIG. 2, underlined sequence). Thus the urinary soluble interferon-gamma receptor fragment was identified as a fragment of the corresponding IFN-gamma cell surface receptor.

3.5 Reversed-phase high pressure liquid chromatography (HPLC)

The reversed-phase HPLC column Aquapore RP 300 4.6×30 mm (Brownlee Labs) was prewashed with 0.3% aqueous trifluoroacetic acid (TFA) (Buffer F)

until a stable baseline was obtained by the fluorescamine detection system. The active fractions eluted from the affinity columns of steps 3.1 and 3.2 and/or 3.3 were pooled and injected in one 1.6 ml portion onto the column. The column was run with Buffer F at a flow rate of 0.5 ml/minute until the fluorometer did not detect any protein. The column was then eluted at a flow rate of 0.5 ml/minute, with a 0-20% linear gradient of acetonitrile in Buffer F for 5 minutes, followed by a 20-90% linear gradient of acetonitrile for 120 minutes. The column was then washed for 15 minutes with 80% acetonitrile. Fractions of 0.5 ml were collected and tested for protein content and for bioactivity. The active proteins elute as a single protein peak.

3.6 Monitoring of the eluted proteins

The eluted proteins from each of the columns were monitored for protein content for bioactivity (neutralization of the antiviral activity of IFN-gamma), for inhibition of binding of $^{125}$I-IFN-gamma to its monoclonal antibodies in a solid phase radioimmunoassay (RIA), for binding in a double antibody ELISA of monoclonal and polyclonal anti-IFN-gamma receptor antibodies, and by Western blotting with antibodies to the IFN-gamma receptor or with labile ligand ($^{125}$I-IFN-gamma).

The bioassay for the IFN-gamma receptor is based on the neutralization of the antiviral activity of IFN-gamma. Samples to be tested for the presence of the IFN-gamma binding protein were diluted two-fold serially, in Eagle's Minimal Essential Medium (MEM) containing 10% fetal calf serum (HEM-CS). WISH cells (ATCC CCL25) were seeded in 96-well flat-bottom microtiter plates ($2\times10^4$ cells/well) with 100 μl MEM-CS. 50 μl aliquots of the serially diluted proteins were applied to each well and the cells were further incubated for 2 hours at 37° C. IFN-gamma (2 units/ml, 50 μl) was added for further incubation of 24 hours at 37° C. Vesicular stomatitis virus was added for a further incubation of 24 hours at 37° C. The extent of cytopathic effect was determined by staining with crystal violet. One neutralizing unit is defined as the amount of protein sufficient for neutralizing one unit of IFN-gamma. The NIH reference standard of IFN-gamma Gg23-901-503 was used in all assays.

Analysis of the purified preparations by SDS-PAGE (sodium dodecyl sulphate polyacrylamide gel electrophoresis) was performed (FIG. 3) under non-reducing conditions, followed by silver staining or electroblotting on nitrocellulose sheets. Samples of the active fractions eluting from the affinity columns or from the reversed phase HPLC, were mixed with 3× concentrated sample buffer without SDS and without β-mercaptoethanol and loaded on a 12% acrylamide gel.

In FIG. 3: lane 1: mixture of molecular weight markers (αlactalbumin 14.4K, soybean trypsin inhibitor 20.1K, carbonic anhydrase 30K, ovalbumin 43K, bovine serum albumin 67K, and phosphorylase b 94K); lane 2: eluate (300 ng) of the immobilized recombinant IFN-gamma column; lane 3: eluate (250 ng) of the anti-IFN-gamma receptor monoclonal antibody column. The gel was run at 160 volt and the protein bands were visualized by silver staining. As shown in lane 2, the purified IFN-gamma fragment moved as a single band, with an apparent molecular weight of 40K. Binding of anti-IFN-gamma receptor monoclonal antibody No. 177-1 was done following SDS-PAGE under non-reducing conditions and electroblotting onto nitrocellulose membrane, performed essentially as the Western blotting method. Lane 4: eluate (600 ng) of the immobilized recombinant IFN-gamma column; lane 5: eluate (900 ng) of anti IFN-gamma receptor monoclonal antibody column; lane 6: eluate (1200 ng) of recombinant interleukin-6 (rIL-6) column (negative control); lane 7: 14C-molecular weight markers. Lanes 4–7 were visualized by autoradiography.

As shown in FIG. 3,lanes 2 and 3, a similar pattern of protein bands was obtained from the eluates of both affinity columns of examples 3.1 and 3.2, corresponding to proteins of molecular weight 40K, 53K and two protein bands of molecular weight higher than 93K. Following electroblotting onto nitrocellulose membrane, only the 40K protein in both preparations reacted specifically with the anti-IFN-gamma receptor monoclonal antibody (FIG. 3, lanes 4 and 5). The same band also reacted specifically with $^{125}$I-IFN-gamma but the signal was faint (data not shown). From the results obtained, it was concluded that the 40K protein is an IFN-gamma receptor fragment containing the ligand binding domain of the IFN-gamma receptor.

Further confirmation that the 40K protein of the invention is a fragment of the IFN-gamma receptor was obtained by two additional tests. The eluate of the recombinant IFN-gamma column of example 3.1 inhibited, in a dose dependent manner, the binding of $^{125}$I-IFN-gamma to anti-IFN-gamma monoclonal antibody 3-3 in a solid phase RIA (FIG. 4*a*). The same eluate gave a specific signal in a double-antibody ELISA based on monoclonal and polyclonal anti-IFN-gamma receptor antibodies (FIG. 4*b*).

FIG. 4*a* shows inhibition of $^{125}$I-IFN-gamma binding in solid phase RIA to its monoclonal antibody by the IFN-gamma binding protein of the eluate of example 3.1. Various concentrations of the eluate were tested for their ability to inhibit the binding of $^{125}$I-IFN-gamma ($2.5\times10^6$ cpm/μg 10,000 cpm) to PVC microtiter plates coated with 5 μg/ml of anti-IFN-gamma monoclonal antibody No. 3-3, disclosed in D. Novick et al. (1983), The EMBO Journal, Vol. 2, No. 9, pp. 1527–1530. Maximal binding with $^{125}$I-IFN-gamma alone was 4300 cpm. Background binding (200 cpm) was determined in the presence of excess unlabeled IFN-gamma and was subtracted from all readings. Immunoaffinity purified IFN-gamma receptor from human placenta (8 μg/ml) was used as a positive control and gave 80% inhibition. Ligand affinity purified IL-6 receptor from urine (10 μg/ml) was used as a negative control and gave only 10% inhibition (Ref: Novick, D. et al., J. IFN Res. 9,315 (1989)).

FIG. 4*b* shows the characterization of the IFN-gamma binding protein of the eluate of example 3.1 as IFN-gamma receptor by a double-antibody ELISA. The eluate was tested for its ability to bind to anti-IFN-gamma receptor antibodies by a double-antibody ELISA. 96-well ELISA plates coated with anti-IFN-gamma receptor monoclonal antibody No. 177-1 (10 μg/ml) and blocked with BSA, were incubated first with various concentrations of the IFN-gamma column eluate of example 3.1, then with rabbit anti-IFN-gamma receptor serum (1:1000, prepared against affinity purified human placental IFN-gamma receptor, and then with goat anti-rabbit antibody conjugated to horseradish peroxidase. The plates were then washed and incubated with a peroxidase substrate and measured by an ELISA reader. Immunoaffinity purified IFN-gamma receptor from human placenta (0.5 μg/ml) was used as a positive control and gave 0.45 $O.D._{600}$. Ligand affinity purified IL-6 receptor from urine (0.5 µg/ml) was used as a negative control and gave 0.06 O.D.$_{600}$.

A further conclusive confirmation of the identity of the 40K protein of the invention as a fragment of the IFN-gamma receptor is shown in example 3.4, by comparison of the sequences of both molecules.

EXAMPLE 4

Genetic Engineering of the Soluble IFN-Gamma Receptor Extracellular Fragment This invention further concerns DNA molecules comprising the nucleotide sequence coding for the IFN-gamma receptor soluble human extracellular fragment, replicable expression vehicles containing said DNA molecules, hosts transformed therewith and the soluble human IFN-gamma receptor extracellular fragment produced by expression of such transformed hosts.

The cloning of the IFN-gamma receptor soluble extracellular fragment may be carried out by different techniques. In a first approach, cDNA clones encoding the IFN-gamma receptor fragment are obtained from a cDNA library. In another approach, the DNA coding for the whole human IFN-gamma receptor is first obtained and then cut by known techniques in order to obtain the DNA sequence coding for the IFN-gamma receptor fragment. According to one approach mRNA is extracted from IFN-gamma receptor producing cells such as WISH or HeLa cells and cDNA is prepared by the use of reverse transcriptase. The cDNA is cut in order to comprise only the sequence of the soluble extracellular fragment and then cloned in an expression vector such as lambda gt 11 and screened by the use of specific antibodies (polyclonal or monoclonal) to the IFN-gamma receptor which are disclosed in U.S. Pat. No. 4,897,264 and U.S. Ser. No. 07/436,328, now abandoned. The lambda gt 11 expression vector can be used for insertion of DNA up to 7 kb in length at a unique EcoRI site 53 bases upstream from the β-galactosidase termination codon. Therefore, foreign sequences of DNA may be inserted into this site and expressed under appropriate conditions as fusion proteins. The lambda gt 11 expression vector is particularly useful for the construction of cDNA libraries to be screened with antibody probes (Huynh, T. V. et al. in: David Glover (ed.), *DNA Cloning Techniques: A Practical Approach*, IRL Press, Oxford (1984) pp. 49-78), as outlined here.

Following another approach, a synthetic oligonucleotide or a mixture of synthetic oligonucleotides, whose sequence is derived from the known sequence, e.g., the N-terminal amino acid sequence of the IFN-gamma receptor, are produced and this oligonucleotide or the mixture of oligonucleotides are used as a probe for cloning the cDNA or the genomic DNA coding for IFN-gamma receptor. These DNA molecules, are then cut in order to comprise the DNA sequence coding for its soluble extracellular fragment and inserted into appropriately constructed expression vectors by techniques well known in the art (see Maniatis et al., op cit.). The DNA coding for the whole receptor may itself be inserted into appropriately constructed expression vectors and then be used to transform eukaryotic cells, which may cleave the protein after expression giving as end product the soluble extracellular receptor fragment of the invention. Double-Stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment with alkaline phosphatase.

In order to be capable of expressing a desired protein, an expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters). They are different for prokaryotic and eukaryotic cells.

The promoters that can be used in the present invention may be either constitutive, for example, the int promoter of bacteriophage lambda, the bla promoter of the β-lactamase gene of pBR322, and the CAT promoter of the chloramphenicol acetyl transferase gene of pPR325, etc., or inducible, such as the prokaryotic promoters including the major right and left promoters of bacteriophage lambda ($P_L$ and $P_R$), the trp, recA, lacZ, lacI, ompF and gal promoters of *E. coli*, or the trp-lac hybrid promoter, etc. (Glick, B. R. (1987) J. Ind. Microbiol. 1:277-282).

Besides the use of strong promoters to generate large quantities of mRNA, in order to achieve high levels of gene expression in prokaryotic cells, it is necessary to use also ribosome-binding sites to ensure that the mRNA is efficiently translated. One example is the Shine-Dalgarno sequence (SD sequence) appropriately positioned from the initiation codon and complementary to the 3'-terminal sequence of 16S RNA.

For eukaryotic hosts, different transcriptional and translational regulatory sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the whole human IFN-gamma receptor or for the IFN-gamma receptor soluble extracellular fragment of the invention preceded by a nucleotide sequence of a signal peptide and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector. The marker may provide for prototrophy to an auxotropic host, biocide resistance, e.g., antibiotics, or heavy metals, such as copper, or the like. The selectable marker gene can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., (1983) Mol. Cel. Biol. 3:280.

In a preferred embodiment, the introduced DNA molecule will be incorporated into a plasmid or viral vector capable of autonomous replication in the recipient host. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids such as those capable of replication in *E. coli*, for example, pBR322, ColEl, pSC101, pACYC 184, etc. (see Maniatis et al., *Molecular Cloning: A Laboratory Manual*, op.-cit.); Bacillus plasmids such as pC194, pC221, pT127, etc. (Gryczan, T., *The Molecular Biology of the Bacilli*, Academic Press, NY (1982), pp. 307-329); Streptomyces plasmids including pIJ101 (Kendall, K. J. et al., (1987) J. Bacteriol. 169:4177-4183); Streptomyces bacteriophages such as φC31 (Chater, K. F. et al., in: *Sixth International Symposium on Actinomycetales Biology*, Akademiai Kaido, Budapest, Hungary (1986), pp. 45-54), and Pseudomonas plasmids (John, J. F., et al. (1986) Rev. Infect. Dis. 8:693-704), and Izaki, K. (1978) Jpn. J. Bacteriol. 33:729-742).

Preferred eukaryotic plasmids include BPV, vaccinia, SV40, 2-micron circle, etc., or their derivatives. Such plasmids are well known in the art (Botstein, D., et al. (1982) Miami Wint. Symp. 19:265-274; Broach, J. R., in: *The Molecular Biology of the Yeast Saccharomyces: Life Cycle and Inheritance*, Cold Spring Harbor Laboratory, Cold Spring Harbor, NY, pp. 445-470 (1981); Broach, J. R., (1982) Cell 28:203-204; Bollon, D. P., et al. (1980) J. Clin. Hematol. Oncol. 10:39-48; Maniatis, T., in: *Cell Biology: A Comprehensive Treatise, Vol. 3: Gene Expression*, Academic Press, NY, pp. 563-608 (1980)).

Once the vector or DNA sequence containing the construct(s) has been prepared for expression, the DNA construct(s) may be introduced into an appropriate host cell by any of a variety of suitable means: transformation, transfection, conjugation, proto-plast fusion, electroporation, calcium phosphate-precipitation, direct microinjection, etc.

Host cells to be used in this invention may be either prokaryotic or eukaryotic. Preferred prokaryotic hosts include bacteria such as *E. coli*, Bacillus, Streptomyces, Pseudomonas, Salmonella, Serratia, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F-, lambda-, prototropic (ATCC 27325)), and other enterobacterium such as Salmonella typhimurium or Serratia marcescens and various Pseudomonas species. Under such conditions, the protein will not be glycosylated. The prokaryotic host must be compatible with the replicon and control sequences in the expression plasmid.

Preferred eukaryotic hosts are mammalian cells, e.g., human, monkey, mouse and chinese hamster ovary (CHO) cells, because they provide post-transolational modifications to protein molecules including correct folding or glycosylation at correct sites or cleavage of the whole receptor molecule to its extracellular fragment. Also yeast and insect cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e. pre-peptides).

After the introduction of the vector, the host cells are grown in a selective medium, which selects for the growth of vector-containing cells. Expression of the cloned gene sequence(s) results in the production of the desired human soluble IFN-gamma receptor extracellular fragment. The expressed protein is then isolated and purified in accordance with the purification method described in the present application or by any other conventional procedure involving extraction, precipitation, chromatography, electrophoresis, or the like.

UTILITY AND COMPOSITIONS

The human soluble IFN-gamma receptor extracellular fragment and salts, functional derivatives, precursors and active fractions thereof are indicated for antagonizing the undesirable effects of IFN-gamma in mammals, i.e. for treating conditions wherein excess of IFN-gamma is formed endogenously or is exogenously administered and provokes malignancies or other disease conditions.

The present invention further relates to pharmaceutical compositions comprising a pharmaceutically acceptable carrier and human soluble IFN-gamma receptor extracellular fragment or a salt, functional derivative, precursor or active fraction thereof, as active ingredient. These compositions may be used in any condition where there is an over production of endogenous IFN-gamma. The way of administration can be via any of the accepted modes of administration for similar agents and will depend on the condition to be trated.

The pharmaceutical compositions of the invention are prepared for administration by mixing the protein or a derivative thereof with physiologically acceptable carriers, stabilizers and excipients, and prepared in dosage form, e.g. by lyophilization in dosage vials. The amount of active compound to be administered will depend on the route of administration, the disease to be treated and the condition of the patient.

Applicants hereby incorporate by reference all publications and patents cited herein, including applicants' Israeli priority application 91562 filed Sep. 7, 1989.

We claim:

1. Process for the production of substantially purified soluble human IFN-gamma receptor extracellular fragment which comprises:
   (a) recovering the crude protein fraction from a dialyzed concentrate of human urine;
   (b) subjecting said crude protein fraction of step (a) to affinity chromatography on a column of immobilized IFN-gamma or on a column of immobilized anti-IFN-gamma receptor monoclonal antibody; and
   (c) recovering the substantially purified soluble IFN-gamma receptor extracellular fragment, said protein having a molecular weight of about 40K on SDS-PAGE under non-reducing conditions.

2. Process according to claim 1 wherein the crude protein fraction of step (a) is subjected to ion exchange chromatography prior to the affinity chromatography of step (b).

3. Process according to claim 1 wherein the active fractions of step (c) are further applied to reversed phase HPLC.

4. Process according to claim 1 wherein the eluate of step (b) from the immobilized anti-IFN-gamma receptor monoclonal antibody column is further purified on an immobilized IFN-gamma column.

* * * * *